(12) United States Patent
Zhou et al.

(10) Patent No.: US 12,325,672 B1
(45) Date of Patent: Jun. 10, 2025

(54) MULTIFUNCTIONAL MICROBIAL AGENT AND APPLICATIONS THEREOF

(71) Applicant: HUBEI MAOSHENG BIOLOGY CO., LTD., Suizhou (CN)

(72) Inventors: Yixin Zhou, Suizhou (CN); Jie Huang, Suizhou (CN); Yu Jiang, Suizhou (CN); Wei Li, Suizhou (CN); Deng Fan, Suizhou (CN); Wanyang Chen, Suizhou (CN); Shibai Zhang, Suizhou (CN)

(73) Assignee: HUBEI MAOSHENG BIOLOGY CO., LTD., Suizhou (CN)

( * ) Notice: Subject to any disclaimer, the term of this patent is extended or adjusted under 35 U.S.C. 154(b) by 0 days.

(21) Appl. No.: 18/985,130

(22) Filed: Dec. 18, 2024

Related U.S. Application Data

(63) Continuation of application No. PCT/CN2024/111585, filed on Aug. 13, 2024.

(30) Foreign Application Priority Data

Dec. 25, 2023 (CN) .......................... 202311798907.2

(51) Int. Cl.
| | |
|---|---|
| C05F 11/08 | (2006.01) |
| A01N 63/25 | (2020.01) |
| A01P 21/00 | (2006.01) |
| C05F 3/00 | (2006.01) |
| C05G 5/40 | (2020.01) |
| C12N 1/20 | (2006.01) |
| C12R 1/01 | (2006.01) |

(52) U.S. Cl.
CPC .............. *C05F 11/08* (2013.01); *A01N 63/25* (2020.01); *A01P 21/00* (2021.08); *C05F 3/00* (2013.01); *C05G 5/40* (2020.02); *C12N 1/205* (2021.05); *C12R 2001/01* (2021.05)

(58) Field of Classification Search
None
See application file for complete search history.

(56) References Cited

U.S. PATENT DOCUMENTS

2023/0159405 A1  5/2023  Villaverde et al.

FOREIGN PATENT DOCUMENTS

| CN | 103194410 A | 7/2013 | |
|---|---|---|---|
| CN | 107721713 A | 2/2018 | |
| CN | 110982740 A | 4/2020 | |
| CN | 113480351 A | 10/2021 | |
| CN | 113980837 A | 1/2022 | |
| CN | 117660237 A | * 3/2024 | ............. A01N 63/20 |
| CN | 117778250 A | 3/2024 | |
| WO | 9909834 A2 | 3/1999 | |

OTHER PUBLICATIONS

GB 7179-87, Method for the determination of soil total nitrogen(Semi-micro Kjeldahl method), China National Standards, 1987, China National Bureau of Standards (CNBS).
NY/T 889-2004, Determination of exchangeable potassium and non-exchangeable potassium content in soil, Agricultural Industry Standard of the People's Republic of China, 2005, Ministry of Agriculture.
NY/T 1121.Jul. 2014, Soil testing—Part 7: Method for determination of available phosphorus in soil, Agricultural Industry Standard of the People's Republic of China, 2014, Ministry of Agriculture of the PRC.

* cited by examiner

*Primary Examiner* — Alton N Pryor
(74) *Attorney, Agent, or Firm* — Bayramoglu Law Offices LLC

(57) ABSTRACT

A multifunctional microbial agent and applications thereof are provided. The multifunctional microbial agent includes a composite microbial liquid and an adsorbable carrier; and the adsorbable carrier includes livestock and poultry manure, germ bran, and straw. Three new *Bacillus* strains with nitrogen-fixing, phosphorus-releasing, and potassium-releasing activities are screened and used as excellent microbial agents to produce strains. The multifunctional microbial agent produced by mixing the microbial liquid and exogenous organic raw materials, livestock and poultry manure and crop straw can better improve the soil microbial environment, activate soil to retain nutrients, promote crop nutrient absorption, and improve crop yield and quality.

20 Claims, No Drawings

MULTIFUNCTIONAL MICROBIAL AGENT AND APPLICATIONS THEREOF

CROSS REFERENCE TO THE RELATED APPLICATIONS

This application is a continuation application of International Application No. PCT/CN2024/111585, filed on Aug. 13, 2024, which is based upon and claims priority to Chinese Patent Application No. 202311798907.2, filed on Dec. 25, 2023, the entire contents of which are incorporated herein by reference.

TECHNICAL FIELD

The present disclosure relates to the technical field of biology engineering, and in particular to a multifunctional microbial agent and applications thereof.

BACKGROUND

Microbial agent is a kind of green environmental protection, and eco-friendly agricultural product, with the advantages of increasing soil fertility, reducing the use of chemical fertilizers and pesticides, purifying and repairing soil, reducing plant diseases, improving quality and increasing production. However, the growth cycle of microorganisms is long, and some strains have strict requirements on the growth environment. Multifunctional microbial agents combined with adsorbable carriers can better meet the environmental and nutritional needs of microbial life, and functional bacteria are prone to colonization and play a role quickly after being applied to the soil.

Agricultural waste mainly includes crop straw and livestock and poultry manure. If it is not properly handled into the environment, it is easy to cause waste of resources and environmental pollution.

The multifunctional microbial agents mainly take livestock and poultry manure, crop straw, etc. as a carrier and combine with microbial lipids, to prepare a microbial agent with simple strains that can efficiently promote plant growth. It can effectively reduce the waste of resources and environmental pollution caused by agricultural waste.

SUMMARY

An objective of the present disclosure is to provide a multifunctional microbial agent and applications thereof.

In order to achieve the above objective, the present disclosure adopts the following technical solutions.

The present disclosure provides a multifunctional microbial agent, including a composite microbial liquid and an adsorbable carrier; and the adsorbable carrier includes livestock and poultry manure, germ bran and straw; and the composite microbial liquid includes: nitrogen-fixing *Paenibacillus mucilaginosus* MSSW01, potassium-releasing *Paenibacillus mucilaginosus* MSSW02 and *Paenibacillus mucilaginosus* MSSW03.

Preferably, a volume ratio of nitrogen-fixing *Paenibacillus mucilaginosus* MSSW01, potassium-releasing *Paenibacillus mucilaginosus* MSSW02 and *Paenibacillus mucilaginosus* MSSW03 is (1-2):(1-2):(1-2).

Preferably, viable counts of the nitrogen-fixing *Paenibacillus mucilaginosus* MSSW01, potassium-releasing *Paenibacillus mucilaginosus* MSSW02 and *Paenibacillus mucilaginosus* MSSW03 are $2\text{-}5 \times 10^9$ cfu·mL$^{-1}$, respectively.

Preferably, a viable count of the composite microbial liquid is $2\text{-}5 \times 10^9$ cfu·mL$^{-1}$.

Preferably, a mass ratio of livestock and poultry manure, germ bran and straw is (25-35):(10-20):(8-12).

Preferably, a mass-volume ratio of the adsorbable carrier to the multifunctional microbial agent is 3-10 g: 1 mL.

Preferably, types of livestock and poultry manure are pig manure, cow manure, sheep manure, chicken manure or duck manure; a type of straw is corn straw; and a water content of the adsorbable carrier is 20-25%.

The present disclosure further provides an application of the multifunctional microbial agent in planting wheat.

The present disclosure further provides an application of the multifunctional microbial agent in fixing nitrogen, releasing potassium or releasing phosphorus for soil.

According to the present disclosure, three new *Bacillus* strains with nitrogen-fixing, phosphorus-releasing and potassium-releasing activities are screened and used as excellent microbial agents to produce strains. The multifunctional microbial agent produced by mixing the microbial liquid and the adsorbable carrier including livestock and poultry manure and crop straw can better improve the soil microbial environment, activate soil to retain nutrients, promote crop nutrient absorption, and improve crop yield and quality.

BRIEF DESCRIPTION OF BIOLOGICAL PRESERVATION

Nitrogen-fixing *Paenibacillus mucilaginosus* MSSW01, Latin for *Paenibacillus mucilaginosus*, the strain is deposited in the China Center for Type Culture Collection, Address: Wuhan University, Wuhan, China, Date of preservation: Aug. 14, 2023, Preservation No: CCTCC NO: M 20231471.

Potassium-releasing *Paenibacillus mucilaginosus* MSSW02, Latin for *Paenibacillus mucilaginosus*, the strain is deposited in the China Center for Type Culture Collection, Address: Wuhan University, Wuhan, China, Date of preservation: Aug. 14, 2023, Preservation No: CCTCC NO: M 20231472.

*Paenibacillus mucilaginosus* MSSW03, Latin for *Paenibacillus mucilaginosus*; and the strain is deposited in the China Center for Type Culture Collection, Address: Wuhan University, Date of preservation: Aug. 14, 2023, Preservation No: CCTCC NO: M 202314713.

DETAILED DESCRIPTION OF THE EMBODIMENTS

In the following, the technical solutions provided by the present disclosure are described in detail in combination with the embodiments, but they cannot be understood as limiting the scope of protection of the present disclosure.

Embodiment 1

A preparation method of a multifunctional microbial agent, including the following steps:

(1) Three strains of *Paenibacillus mucilaginosus* MSSW03 (a viable count of $3 \times 10^9$ cfu·mL$^{-1}$), potassium-releasing *Paenibacillus mucilaginosus* MSSW02 (a viable count of $3 \times 10^9$ cfu mL$^{-1}$), nitrogen-fixing *Paenibacillus mucilaginosus* MSSW01 (a viable count of $3 \times 10^9$ cfu·mL$^{-1}$)

were mixed according to a volume ratio of 1:1:1, to obtain a multifunctional microbial agent (a viable count of $3\times10^9$ cfu·mL$^{-1}$).

(2) Pig manure, grem bran and crop straw were mixed and added in a stirring mixer at a mass ratio of 30:15:10, a water content was adjusted to 23%, and a mixture was obtained as an adsorbable carrier. Then, according to a mass-volume ratio of 7 g:1 mL, the multifunctional microbial agent obtained by step (1) was added, and a multifunctional microbial agent product was obtained by fully stirring and mixing. A viable count of the multifunctional microbial agent was not less than $5\times10^8$ cfu·mL$^{-1}$.

Embodiment 2

(1) Taking wheat as an example, the growth-promoting effect of multifunctional microbial agents on crops was explored.

In plastic flowerpots with a length and width of 10 cm, the farmland soil was uniformly added and compacted to 1.5 cm away from the mouth of each flowerpot, 25 wheat seeds of approximately the same size were evenly placed into the soil, the soil was covered to the mouth of each flowerpot, an appropriate amount of water was added to maintain consistent humidity in the soil of each flowerpot, and a daily watering amount of each flowerpot was controlled to be the same. In the later stage, each flowerpot was watered every 2 days.

One week after emergence, the multifunctional microbial agents in Embodiment 1 were inoculated by watering. Specifically, 10 g of multifunctional microbial agents were accurately weighed and dissolved in 90 mL of sterile physiological saline. 1 mL of the solution was taken and diluted with 9 mL of sterile physiological saline for application, and each flowerpot was inoculated with 5 mL. Each treatment was set up 5 replicates. A potted plant without being inoculated by the multifunctional microbial agents was used as a black control group, and other commercially available multifunctional microbial inoculant products (Guangxi Agricultural Bioengineering Co., Ltd.; and the microbial agent (agricultural special) *Bacillus subtilis*) was used as a positive control group.

Culture conditions: outdoor culture, watering with distilled water, and harvesting after 30 days.

After sowing for 30 days and harvesting, the whole plant of wheat in the flowerpot was carefully pulled out, most of the soil that stuck to the root was shaken off, then the whole plant of wheat was washed with tap water and wiped dry with newspaper, being laid flat on a table in turn, and a length from the cotyledon node to the growth point was measured with a ruler as a plant height of wheat.

A length of the third true cotyledon was measured with a ruler as a leaf length of wheat.

Each wheat plant was washed and wiped dry, and a number of roots elongated in the embryo of wheat seeds was counted as a number of seed roots.

A length from the root-stem junction of wheat to the longest root tip of the whole plant, i.e., the longest root length of seed embryo, was measured as the maximum root length.

After each wheat plant was washed and wiped dry, the fresh weight was measured by direct weighing with a balance (accurate to 0.01 g).

Then each wheat plant was dried in an oven, dried at 100° C. to constant weight, and the dry weight was measured. The above data was recorded, as shown in Table 1.

TABLE 1

Effects of different treatments on wheat traits

| Treatment | Plant height (cm) | Leaf length (cm) | Maximum root length (cm) | Fresh weight (g) | Dry weight (g) |
|---|---|---|---|---|---|
| Blank control group (ck) | 29.3 ± 1.5 | 9.7 ± 0.3 | 10.9 ± 0.2 | 9.5 ± 1.3 | 1.5 ± 0.1 |
| Experimental group | 34.5 ± 1.4 | 13.8 ± 0.4 | 14.5 ± 0.1 | 14.8 ± 0.9 | 3.5 ± 0.2 |
| Positive control group | 34.1 ± 1.2 | 13.5 ± 0.3 | 13.2 ± 0.3 | 14.4 ± 1.0 | 3.1 ± 0.1 |

According to Table 1, compared with the blank control group, the plant height, leaf length, maximum root length, fresh weight and dry weight of wheat inoculated with the multifunctional microbial agents produced by the present disclosure were significantly increased by 17.75%, 42.27%, 33.03%, 55.79% and 133.33%, respectively, and were increased by 1.17%, 2.22%, 9.85%, 2.70% and 9.30%, respectively compared with other commercially available multifunctional microbial agents. The multifunctional microbial agents produced by the present disclosure had a significant effect on promoting the growth of wheat and had great market potential.

(2) Experiment of Measuring Soil Physical and Chemical Properties

After sowing for 30 days and harvesting in step (1), the potting soil of each test group was collected respectively, dried naturally, sieved and packed into plastic bags. The pH, and contents of organic matter, total nitrogen, rapidly available potassium and available phosphorus were determined, and the soil without planting wheat was used as an original soil group. Data was recorded, as shown in Table 2.

Determination of total nitrogen content in soil: referring to NY/T 53-1987 "Soil Total Nitrogen Determination Method (Semi-micro Kjeldahl Method)", under the action of sodium thiosulfate, concentrated sulfuric acid, perchloric acid and catalyst, it was completely converted into ammonium nitrogen by redox reaction. The ammonia from the digested solution after alkalization distillation was absorbed by boric acid, and titrated with standard hydrochloric acid solution, and the total nitrogen content in the soil was calculated according to the amount of standard hydrochloric acid solution.

Determination of rapidly available potassium in soil: referring to NY/T 889-2004 "Determination of Soil Rapidly Available Potassium and Slowly Available Potassium Content", 5 g air-dried soil sample passing through 1 m aperture sieve was weighed and put in a 100 mL triangular flask, 50.0 mL of ammonium acetate solution (soil-liquid ratio of 1:10) was added, the bottle stopper was covered tightly, being shaken at 150 r/min-180 r/min for 30 min at 20° C.-25° C., and dry filtering. The filtrate was measured directly on a flame photometer.

Determination of soil available phosphorus: referring to NY/T 1121.7-2014 "Soil Testing-Part 7: Determination of soil Available Phosphorus", available phosphorus in soil was extracted with 0.5 mol/L sodium bicarbonate solution (pH=8.5). Phosphorus in the extract reacted with molybdenum antimony anti-color reagent to form phosphorus molybdenum blue, and the absorbance was measured at a wavelength of 880 m. In a certain concentration range, the content of phosphorus and the absorbance value conformed to Lambert-Beer's law.

TABLE 2

Effects of applying multifunctional microbial agents on soil fertility

| Treatment | pH | Total nitrogen content (mg · kg$^{-1}$) | Available phosphorus content (mg · kg$^{-1}$) | Rapidly available potassium content (mg · kg$^{-1}$) | organic matter content (g · kg$^{-1}$) |
|---|---|---|---|---|---|
| Original soil | 7.5 | 15.7 ± 0.9 | 15.7 ± 0.9 | 15.7 ± 0.9 | 9.3 ± 0.2 |
| Blank control group | 7.5 | 25.0 ± 2.3 | 20.2 ± 0.9 | 30.7 ± 0.9 | 36.8 ± 1.3 |
| Experimental group | 7.4 | 97.8 ± 0.9 | 80.5 ± 1.0 | 117.8 ± 1.0 | 50.3 ± 2.7 |
| Other commercially available multifunctional microbial agents | 7.4 | 96.4 ± 2.5 | 78.9 ± 1.2 | 116.2 ± 1.2 | 48.2 ± 2.3 |

The experimental results were shown in Table 2. After the end of the step (1) experiment, indexes were detected on the pot soil, it was found that nutritional indexes in the soil with the application of multifunctional microbial agents were greatly improved, wherein compared with the blank control group, the total nitrogen content was increased by 291.20%, the available phosphorus content was increased by 298.51%, the rapidly available potassium content was increased by 283.71%, and the organic matter content was increased by 36.68%, compared with other commercially available multifunctional microbial agents, they were increased by 1.45%, 2.02%, 1.38%, and 4.36%, respectively.

The above descriptions are only the preferred embodiments of the present disclosure. It is to be pointed out that those of ordinary skill in the art can also make several improvements and modifications without departing from the principle of the present disclosure, and such improvements and modifications shall fall within the protection scope of the present disclosure.

What is claimed is:

1. A multifunctional microbial agent, comprising a composite microbial liquid and an adsorbable carrier; wherein the adsorbable carrier comprises livestock and poultry manure, germ bran, and straw; and
   the composite microbial liquid comprises: nitrogen-fixing *Paenibacillus mucilaginosus* MSSW01, potassium-releasing *Paenibacillus mucilaginosus* MSSW02, and *Paenibacillus mucilaginosus* MSSW03; wherein
   a preservation number of the nitrogen-fixing *Paenibacillus mucilaginosus* MSSW01 is CCTCC NO: M 20231471;
   a preservation number of the potassium-releasing *Paenibacillus mucilaginosus* MSSW02 is CCTCC NO: M 20231472;
   a preservation number of the *Paenibacillus mucilaginosus* MSSW03 is CCTCC NO: M 20231473; and
   a volume ratio of the nitrogen-fixing *Paenibacillus mucilaginosus* MSSW01, the potassium-releasing *Paenibacillus mucilaginosus* MSSW02, and the *Paenibacillus mucilaginosus* MSSW03 is (1-2):(1-2):(1-2).

2. The multifunctional microbial agent according to claim 1, wherein types of the livestock and poultry manure are pig manure, cow manure, sheep manure, chicken manure, or duck manure.

3. The multifunctional microbial agent according to claim 1, wherein viable counts of the nitrogen-fixing *Paenibacillus mucilaginosus* MSSW01, the potassium-releasing *Paenibacillus mucilaginosus* MSSW02, and the *Paenibacillus mucilaginosus* MSSW03 are 2-5×10$^9$ cfu·mL$^{-1}$, respectively.

4. The multifunctional microbial agent according to claim 1, wherein a viable count of the composite microbial liquid is 2-5×10$^9$ cfu·mL$^{-1}$.

5. The multifunctional microbial agent according to claim 1, wherein a mass ratio of the livestock and poultry manure, the germ bran, and the straw is (25-35):(10-20):(8-12).

6. The multifunctional microbial agent according to claim 1, wherein a mass-volume ratio of the adsorbable carrier to the multifunctional microbial agent is 3-10 g: 1 mL.

7. The multifunctional microbial agent according to claim 1, wherein a type of the straw is corn straw; and a water content of the adsorbable carrier is 20-25%.

8. An application of the multifunctional microbial agent according to claim 1 in planting wheat.

9. An application of the multifunctional microbial agent according to claim 1 in fixing nitrogen, releasing potassium, or releasing phosphorus for soil.

10. The application according to claim 8, wherein in the multifunctional microbial agent, types of the livestock and poultry manure are pig manure, cow manure, sheep manure, chicken manure, or duck manure.

11. The application according to claim 8, wherein in the multifunctional microbial agent, viable counts of the nitrogen-fixing *Paenibacillus mucilaginosus* MSSW01, the potassium-releasing *Paenibacillus mucilaginosus* MSSW02, and the *Paenibacillus mucilaginosus* MSSW03 are 2-5×10$^9$ cfu mL$^{-1}$, respectively.

12. The application according to claim 8, wherein in the multifunctional microbial agent, a viable count of the composite microbial liquid is 2-5×10$^9$ cfu·mL$^{-1}$.

13. The application according to claim 8, wherein in the multifunctional microbial agent, a mass ratio of the livestock and poultry manure, the germ bran, and the straw is (25-35):(10-20):(8-12).

14. The application according to claim 8, wherein in the multifunctional microbial agent, a mass-volume ratio of the adsorbable carrier to the multifunctional microbial agent is 3-10 g: 1 mL.

15. The application according to claim 8, wherein in the multifunctional microbial agent, a type of the straw is corn straw; and a water content of the adsorbable carrier is 20-25%.

16. The application according to claim 9, wherein in the multifunctional microbial agent, types of the livestock and poultry manure are pig manure, cow manure, sheep manure, chicken manure, or duck manure.

17. The application according to claim 9, wherein in the multifunctional microbial agent, viable counts of the nitrogen-fixing *Paenibacillus mucilaginosus* MSSW01, the potassium-releasing *Paenibacillus mucilaginosus* MSSW02, and the *Paenibacillus mucilaginosus* MSSW03 are 2-5×10$^9$ cfu·mL$^{-1}$, respectively.

18. The application according to claim 9, wherein in the multifunctional microbial agent, a viable count of the composite microbial liquid is 2-5×10$^9$ cfu·mL$^{-1}$.

19. The application according to claim 9, wherein in the multifunctional microbial agent, a mass ratio of the livestock and poultry manure, the germ bran, and the straw is (25-35):(10-20):(8-12).

20. The application according to claim 9, wherein in the multifunctional microbial agent, a mass-volume ratio of the adsorbable carrier to the multifunctional microbial agent is 3-10 g: 1 mL.

* * * * *